US00PP22363P2

(12) United States Plant Patent
Podaras

(10) Patent No.: US PP22,363 P2
(45) Date of Patent: Dec. 20, 2011

(54) ***PHYSOCARPUS* PLANT NAMED 'PODARAS 2'**

(50) Latin Name: *Physocarpus opulifolius*
Varietal Denomination: Podaras 2

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,653

(22) Filed: Mar. 2, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP11,211 P * 2/2000 Kordes et al. ..... Plt./226
* cited by examiner

*Primary Examiner* — Susan McCormick Ewoldt
(74) *Attorney, Agent, or Firm* — C. A. Whealy

(57) ABSTRACT

A new and distinct cultivar of *Physocarpus* plant named 'Podaras 2', characterized by its compact and upright plant habit; freely branching habit; dense and bushy habit; dark green-colored leaves; and good garden performance.

1 Drawing Sheet

Botanical designation: *Physocarpus opulifolius.*
Cultivar denomination: 'PODARAS 2'.

BACKGROUND OF THE INVENTION

The present invention relates to a new and distinct cultivar of *Physocarpus* plant, botanically known as *Physocarpus opulifolius* and hereinafter referred to by the name 'Podaras 2'.

The new *Physocarpus* plant is a product of a controlled breeding program conducted by the Inventor in Ithaca, N.Y. The objective of the breeding program is to create new compact *Physocarpus* plants with unique foliage colors, types and textures.

The new *Physocarpus* plant originated from an open-pollination on May 10, 2006 of an unnamed seedling selection of *Physocarpus opulifolius*, not patented, as the female, or seed, parent with an unknown selection of *Physocarpus opulifolius*, as the male, or pollen, parent. The new *Physocarpus* plant was discovered and selected by the Inventor in August, 2008 as a single flowering plant within the progeny of the stated open-pollination in a controlled environment in Ithaca, N.Y.

Asexual reproduction of the new *Physocarpus* plant by cuttings in a controlled environment in West Chicago, Ill. since February, 2009 has shown that the unique features of this new *Physocarpus* plant are stable and reproduced true to type in successive generations of asexual reproduction.

SUMMARY OF THE INVENTION

Plants of the new *Physocarpus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras 2'. These characteristics in combination distinguish 'Podaras 2' as a new and distinct cultivar of *Physocarpus:*

1. Compact and upright plant habit.
2. Freely branching habit; dense and bushy habit.
3. Dark green-colored leaves.
4. Good garden performance.

Plants of the new *Physocarpus* can be compared to plants of the female parent selection. Plants of the new *Physocarpus* differ from plants of the female parent selection in the following characteristics:

1. Plants of the new *Physocarpus* are more compact than plants of the female parent selection.
2. Plants of the new *Physocarpus* and the female parent selection differ in leaf color as plants of the female parent selection have bronze-colored leaves.

Plants of the new *Physocarpus* can be compared to plants of the *Physocarpus opulifolius* 'Diablo', not patented. In side-by-side comparisons, plants of the new *Physocarpus* differed from plants of 'Diablo' in the following characteristics:

1. Plants of the new *Physocarpus* were shorter than plants of 'Diablo'.
2. Plants of the new *Physocarpus* and 'Diablo' differed in leaf color as plants of 'Diablo' had dark burgundy-colored leaves.

BRIEF DESCRIPTION OF THE PHOTOGRAPHS

The accompanying colored photographs illustrate the overall appearance of the new *Physocarpus* plant showing the colors as true as it is reasonably possible to obtain in colored reproductions of this type. Colors in the photographs may differ slightly from the color values cited in the detailed botanical description which accurately describe the colors of the new *Physocarpus* plant.

The photograph at the top of the sheet comprises a side perspective view of a typical plant of 'Podaras 2' grown in a container.

The photograph at the bottom of the sheet is a close-up view of a typical plant of 'Podaras 2 '.

DETAILED BOTANICAL DESCRIPTION

The aforementioned photographs and following observations, measurements and values describe plants grown during the spring and summer in one-gallon containers in an outdoor nursery in Abbotsford, British Columbia, Canada and under commercial practice. Plants were six months old when the photographs and description were taken. In the following description, color references are made to The Royal Horticultural Society Colour Chart, 2007 Edition, except where general terms of ordinary dictionary significance are used.

Botanical classification: *Physocarpus opulifolius* 'Podaras 2'.

Parentage:

*Female, or seed, parent.*—Unnamed seedling selection of *Physocarpus opulifolius*, not patented.

*Male, or pollen, parent.*—Unknown selection of *Physocarpus opulifolius*, not patented.

Propagation:

*Type.*—By cuttings.

*Time to initiate roots plant.*—About two weeks at temperatures of 18° C. to 24° C.

*Time to produce a rooted plant, summer.*—About three weeks at temperatures of 18° C. to 24° C.

*Time to produce a rooted plant, winter.*—About three to four weeks at temperatures of 18° C. to 24° C.

*Root description.*—Fibrous, fine; white in color.

*Rooting habit.*—Freely branching; moderately dense.

Plant description:

*Plant form and growth habit.*—Perennial shrub; compact and upright plant habit; moderately vigorous growth habit.

*Branching habit.*—Freely branching habit with about three lateral branches develop per plant; pinching enhances lateral branch development.

*Plant height.*—About 22.5 cm.

*Plant diameter* (*area of spread*).—About 16 cm by 19 cm.

Lateral branch description:

*Length.*—About 19.7 cm.

*Diameter.*—About 3 cm.

*Internode length.*—About 3.4 cm.

*Texture.*—Smooth, glabrous.

*Color.*—Close to 187A.

Foliage description:

*Arrangement.*—Alternate, simple.

*Length.*—About 6.8 cm.

*Width.*—About 6.4 cm.

*Shape.*—Somewhat deltoid with three lobes; maple leaf-shaped.

*Apex.*—Acute.

*Base.*—Cordate.

*Margin.*—Crenate and serrate.

*Texture, upper and lower surfaces.*—Smooth, glabrous; rugose.

*Venation pattern.*—Palmate and pinnate.

*Color.*—Developing leaves, upper surface: Darker than 147A. Developing leaves, lower surface: Close to 147B. Fully expanded leaves, upper surface: Close to 147A; venation, close to 148A. Fully expanded leaves, lower surface: Close to 148A; venation, close to 147C.

*Petiole.*—Length: About 1.6 cm. Diameter: About 2 mm. Texture, upper and lower surfaces: Smooth, glabrous. Color, upper surface: Close to N199B. Color, lower surface: Close to 199B.

Flower description: Flower initiation and development has not been observed on plants of the new *Physocarpus*.

Garden performance: Plants of the new *Physocarpus* have been observed to have good garden performance.

Pathogen/pest resistance: Plants of the new *Physocarpus* have not been observed to resistant to pathogens and pests common to *Physocarpus*.

It is claimed:

1. A new and distinct *Physocarpus* plant named 'Podaras 2' as illustrated and described.

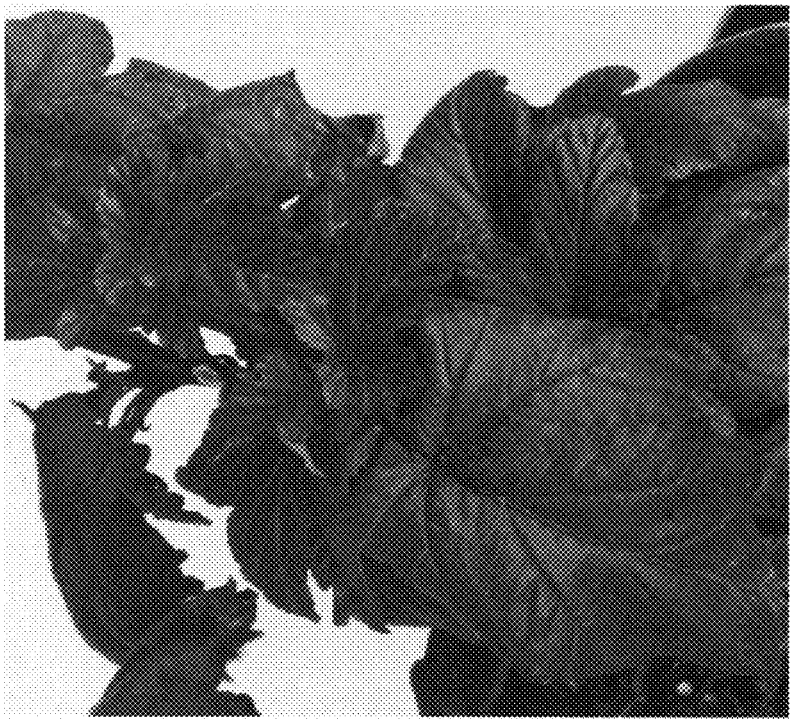
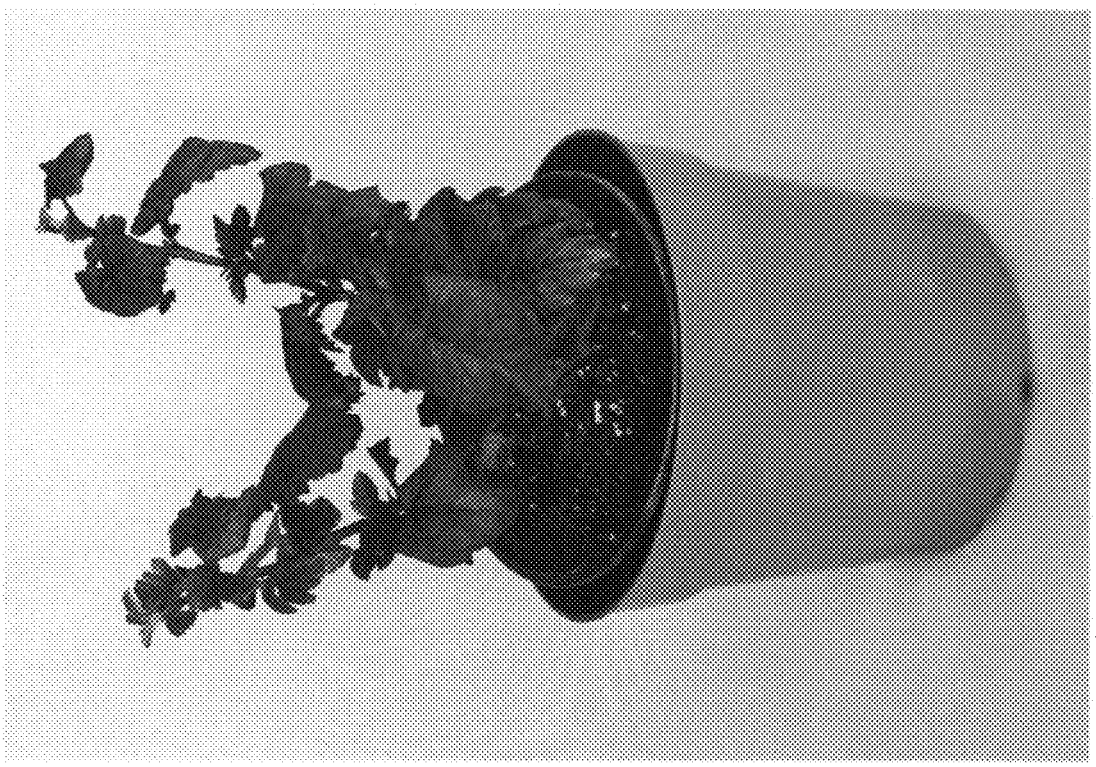

* * * * *